United States Patent [19]

Gaffar et al.

[11] 3,931,398
[45] Jan. 6, 1976

[54] METHOD FOR LOCAL IMMUNIZATION AGAINST DENTAL CARIES

[75] Inventors: Abdul Gaffar, Somerset; Hans Wilhelm Marcussen, Jr., Piscataway, both of N.J.

[73] Assignee: Colgate-Palmolive Company, New York, N.Y.

[22] Filed: June 20, 1973

[21] Appl. No.: 371,842

[52] U.S. Cl. .................................... 424/92; 424/50
[51] Int. Cl.² A61K 39/02; A61K 5/00; A61K 7/26
[58] Field of Search ........................ 424/50, 92

[56] References Cited
FOREIGN PATENTS OR APPLICATIONS
2,212,739  10/1972  Germany .............................. 424/92

OTHER PUBLICATIONS

Chemical Abstracts (1), Vol. 76, entry 135,658k, 1972.
Chemical Abstracts (2), Vol. 77, entry 3696g, 1972.
Chemical Abstracts (3), Vol. 78, entry 95990v, 1973.
Hayashi et al., J. Dent. Res., Vol. 51, pp. 436–442, Mar.–Apr., 1972.

Primary Examiner—Shep K. Rose
Attorney, Agent, or Firm—Steven J. Baron; Robert L. Stone; Herbert S. Sylvester

[57] ABSTRACT

Immunization against dental caries by local administration, in the vicinity of the oral mucosa of an animal susceptible to dental caries, of a vaccine containing a polyfructan or polyglucan polysaccharide, or a levansucrase or dextransucrase enzyme. The polysaccharides may be administered in purified form, or may be in the form of dead cells of the streptococci by which they are elaborated. Polyglucan polysaccharides so useful are produced by elaboration of strains of the species *S.mutans* and *S.sanguis*, while the polyfructan which may be incorporated in the vaccine may be an elaboration product of *Streptomyces Strain SS2*.

10 Claims, No Drawings

METHOD FOR LOCAL IMMUNIZATION AGAINST DENTAL CARIES

BACKGROUND OF THE INVENTION

This invention relates to the prevention of dental caries, and more particularly to a method for immunization against caries employing either of two polysaccharides which are involved, together with the microorganisms by which they are elaborated, in caries formation; or utilizing the corresponding enzymes responsible for the biosynthesis of such polysaccharides.

Recent studies have indicated that the formation of carious lesions on teeth is related to the interaction between carbohydrates (notably sucrose) in the diet and specific bacteria on tooth surfaces. The cariogenic bacteria, predominantly streptococci, adhere to the surfaces of teeth by synthesizing extracellular polysaccharides from the sucrose. These polymers, which are generally either polyglucans or polyfructans (levan), "glue" the bacterial cells together and help them adhere to the teeth. The polysaccharides thus promote action between the bacteria and further sucrose ingested by the host animal and thereby facilitate the formation of further polysaccharides. Moreover, the extracellular polysaccharides thus produced are believed to play significant roles in plaque formation and in the consequent development of caries.

A number of vaccines have been proposed for immunization against dental caries in animals. Various of these proposals are summarized in the copending application of Gaffar and Kestenbaum for "Vaccines for the Prevention of Dental Caries," Ser. No. 360,964 filed May 16, 1973, now U.S. Pat. No. 3,879,545 issued on Apr. 22, 1972 as a continuation-in-part of their prior application Ser. No. 126,933 filed Mar. 22, 1971 and now abandoned. This copending application, the disclosure of which is incorporated by reference herein, relates to caries-preventive vaccines incorporating as the active ingredient thereof a polyfructan (or levan) polysaccharide produced by elaboration of certain strains of streptococcus, particularly Streptococcus Strain SS2. This immunization technique has been found to result in the formation of antibodies against the heterogeneous microorganisms in the recticuloendothelial system and in the blood, and to result in significant decreases in the formation of carious lesions in host animals subjected to inoculation with such organisms.

It is a principal object of the present invention to provide an improved method for immunization against dental caries, utilizing vaccines incorporating the polysaccharide of the aforesaid copending application, another polysaccharide believed to be involved in the formation of dental plaque, or enzymes involved in the synthesis of both such polysaccharides, which method results in markedly decreased caries formation. Other objects and advantages of this invention will be apparent from the following detailed description of preferred embodiments thereof.

SUMMARY OF THE INVENTION

It has been found in accordance with the present invention that improved protection against dental caries with minimum side effects may be achieved by the local administration of particular anti-caries vaccines in the vicinity of the oral mucosa of the animal to be immunized. The vaccines so utilized suitably comprise aqueous saline dispersions of either (1) a polysaccharide elaboration product of a cariogenic microorganism, selected from among the polyfructans and the polyglucans, or (2) an enzyme involved in the synthesis of these polysaccharides, selected from among levansucrase (fructosyl transferase) and dextransucrase (glucosyl transferase).

The immunization technique of the aforesaid copending application is systemic, i.e., the vaccine is injected subcutaneously, intraperitoneally or intravenously. Antibodies formed in this manner are predominantly of the IgM and IgG classes of immunoglobulins. On the other hand, it has been found that the local administration of a caries vaccine in accordance with the present invention primarily stimulates production of antibodies of the IgA type. The IgA immunoglobulins formed locally in the region of the oral mucosa possess a characteristic polypeptide chain referred to as a secretory or transport "piece" which appears to impart increased resistance to proteolytic degradation. See Advances in Immunology, Vol. 9, 1968, chapter entitled "Secretory Immunoglobulins." While the actual mechanism is not known (compare pages 67–69 of Advances in Immunology, supra), it is believed that the IgA-type antibodies assist in controlling bacterial and viral infection in the oral cavity by inhibiting adhesion of the bacteria to the tooth surfaces, thereby impairing plaque formation and the consequent development of caries. Thus, local administration of the noted vaccines provides improved resistance to caries.

As indicated hereinabove, animals susceptible to dental caries are immunized, utilizing the present technique, by local administration of a vaccine in the vicinity of the oral mucosa of the animal. The vaccines locally administered by the method hereof may comprise, as the active ingredient thereof, a polysaccharide elaboration product of a cariogenic Streptococcus organism, i.e., a polyglucan elaboration product of a strain of *S.mutans* or a strain of *S.sanguis;* or a polyfructan (levan) elaboration product of, for example, Streptococcus Strain SS2. Alternatively, it has been found that the enzymes involved in the synthesis of the noted polysaccharides, i.e., dextransucrase and levansucrase, are effective immunizing agents against caries when administered locally in the vicinity of the oral mucosa in accordance with the present invention.

These results are to be contrasted with those obtained upon systemic application of the noted polysaccharides and enzyme transferases; as described in the aforesaid copending application, solely the polyfructan (levan) polysaccharide has been found to effectively immunize against caries when administered by subcutaneous, intraperitoneal or intravenous injection. On the other hand, the local administration of dextransucrase or levansucrase-containing vaccines should also be distinguished from experiments involving similar application of glycosidic hydrolases (see "Immunization with Dextransucrase and Glycosidic Hydrolases," J. A. Hayashi, I. L. Shklair and A. N. Bahn, J. Dent. Res., 51, pp. 436–442, March and April 1972; and Helv. Odont. Acta, 15, No. 2, p. 96, 1971). It has been suggested that the latter enzymes may be a further microbial factor assisting in dental plaque formation by cleaving sialic acid from glycoprotein, the residual protein being precipitated on the surfaces of the teeth and aiding in the build-up of plaque. Apart from the fact that this theory has not met with acceptance in the field, it is clear that the mechanism by which glycosidic hydrolases may participate in plaque and caries formation is quite different from that believed to be applicable to dextransucrase and levansucrase.

PREFERRED EMBODIMENTS OF THE INVENTION

When a polyglucan or polyfructan polysaccharide is employed as the active ingredient of the vaccine hereof, it may be utilized in crude or purified form, or in the form of dead cells of the microorganism by which it is elaborated. The microorganism strains used for this purpose may be cultured and the elaboration products recovered and purified in a manner known per se in the art. In the case of the polyfructan, for example, such is suitably obtained by the elaboration of Streptococcus Strain SS2 as more fully set forth in the aforesaid copending application. The polyfructan or levan polysaccharide thus obtained, after purification by recovery of the higher molecular weight fraction thereof, has characteristic infrared absorption peaks at 920 cm.$^{-1}$, 875 cm.$^{-1}$ and 805 cm.$^{-1}$, an intrinsic viscosity at 25° C of from 0.15 to 0.16, and $[\alpha]_D^{20}$ rotation of 43° to 54°.

When, on the other hand, a vaccine is utilized incorporating a polyglucan as the active ingredient thereof, such may be obtained by elaboration of any of the known strains of *S.mutans*, e.g., Strains 6715 GS-5, FA-1, AHT, or BHT. The polyglucan may be produced therefrom, recovered and purified in accordance with techniques which are well known in the art.

Alternatively, when it is desired to employ the dextransucrase or levansucrase enzymes as the active ingredient of the vaccines utilized in the present method, such may also be used in either crude or purified form, as desired. Techniques for obtaining purified forms of these enzymes which may be utilized in the method hereof are described in the literature; see, for example, J. Carlsson, Caries Research, 4, pages 97–113 (1970); and B. Guggenheim and E. Newburn, Hel. Odont. Acta. 13, pages 84–97 (1969).

The vaccines utilized herein are liquid, preferably aqueous, solutions, emulsions or aerosols containing one or more of the above active ingredients in an amount effective for immunization of the caries-susceptible animal to be immunized. Suitably, from about 0.1 to 1, and preferably from about 0.4 to 0.6, grams of the polyfructan or polyglucan polysaccharide, or levansucrase or dextransucrase enzyme, are dispersed in the liquid vehicle, the amounts of the respective active ingredients being based on the purified forms thereof. The liquid vehicle is preferably sterile saline solution, which may, desirably, be modified by adjuvants such as Freund's adjuvant, complete or incomplete, (in which case emulsions are obtained) or the like. When Freund's adjuvant is so employed, it is suitably incorporated in the vaccine in equal proportions with the active ingredient. Isotonic salts which may also be incorporated in the vaccine include the normal salts used in the preparation of saline solutions, e.g., sodium or potassium chloride. Other adjuvants such as aluminum phosphate, calcium alginate or the like, or other carriers for conjugating the active ingredient(s) in the vaccine, may also be incorporated therein.

Local administration of the vaccine in the vicinity of the oral mucosa may be achieved by direct injection of the vaccine into or near the salivary glands (the major or minor glands), or around the mucous membranes or the areas adjacent the oral cavity, including the chin, of the animal to be immunized. Suitably, the vaccine is administered in dosage levels equivalent to about 1 to 20 micrograms, preferably from about 5 to 10 micrograms, of the active ingredient per kilogram of body weight of the animal to be immunized. Booster shots may also be administered from time to time as necessary.

The following examples are given to further illustrate preferred forms of the present invention:

EXAMPLE 1

Local Administration of Vaccines Containing Polyglucan Polysaccharide Elaboration Product of Strep. mutans The purpose of this experiment was to evaluate the effect of local administration of a vaccine incorporating as the active ingredient thereof a polyglucan isolated from caries-producing *Streptococcus mutans* Strain 6715, the vaccine being injected locally (under the chin) in golden hamsters derived from the National Institute of Health colony.

The polyglucan was prepared from *Strep. mutans* 6715 by the method of A. Jeanes, Methods in Carbohydrate Chemistry, Vol. 5, page 118, Academic Press, New York. The infrared spectra of the polysaccharide isolated peaked at 915, 840, 795, and 770 cm.$^{-1}$. These peaks corresponded to a known sample of polyglucan. The presence of a peak at 795 cm.$^{-1}$ is indicative of a substantial proportion of an $\alpha$, 1,3 linkage in the polysaccharide. When hydrolyzed with 0.20 N $H_2SO_4$ at 100° C for 45 minutes and later examined by thin layer chromatography, only glucose was detected. The polyglucan thus prepared was dissolved in a saline solution containing incomplete Freund's adjuvant in a 1 to 1 ratio.

The experimental animals were divided into three test groups, each of which was placed on the Mitchell cariogenic diet and deionized water. The normal gram-positive flora of each of the hamsters were depressed at weaning by incorporating in the Mitchell diet 100 units of penicillin per gram thereof for a period of four consecutive days. On the fifth day the antibiotic was discontinued, and the animals in each of the test groups were inoculated, in the chin, with *Streptococcus mutans* 6715, maintained on Trypticase soy broth without dextrose (BBL) supplemented with 0.5 percent sucrose and grown anaerobically in an atmosphere of 90 percent hydrogen and 10 percent carbon dioxide at 37° C).

On the day of inoculation the animals in test Group III were immunized with the aforesaid polyglucan-containing vaccine by injection in the chin region. The animals in the diet control, Group I, were not immunized; the further control group, Group II, was solely immunized with the Freund adjuvant.

Four additional injections of the polyglucan-containing vaccine were given at approximately two-week intervals, the successive injections incorporating decreasing concentrations (1 milligram, 150 micrograms, 100 micrograms and 100 micrograms per milliliter, respectively) of the polyglucan. After a period of 12 weeks, the test animals were sacrificed. The animal heads were then defleshed by the well known method of Russell and scored for dental caries by a modified Keyes method. The second and third maxillary molars were utilized in the caries scoring procedure.

The dental caries results thus obtained are summarized below:

| Group | Cariogenic Inoculation | Immunization | Mean Caries Scores |
|---|---|---|---|
| I (9 animals) | S.mutans 6715 | None (diet control) | 45.00 |
| II (9 animals) | S.mutans 6715 | Adjuvant control | 50.60 |
| III (9 animals) | S.mutans 6715 | Polyglucan plus adjuvant vaccine | 29.30 |

The preceding results indicate that the animals subjected to local administration of the polyglucan-containing vaccine (Group III), the inoculated and immunized group, exhibited 38% less caries than the adjuvant congrol group (Group II).

EXAMPLE 2

Local Administration of Vaccine Containing Dextransucrase and Levansucrase Enzymes The purpose of this experiment was to study the effect of local immunization with dextransucrase and levansucrase on caries formation.

Somewhat impure dextransucrase was prepared by the method of Guggenheim and Newburn, supra, from the supernatant liquid of 18-hour cultures of S.mutans 6715 grown on 8 percent sucrose. The preparation had 10 units of dextransucrase activity per mg. of protein, one unit of the enzyme being defined as the amount required to catalyze transformation of 1 mg. of sucrose to dextran in 1 hour (releasing 0.52 mg. of fructose) at pH 6.8. The activity was measured by determining the amount of released reducing sugars.

Somewhat impure levansucrase was prepared by the method of Carlsson, supra, from the supernatant liquid of 18-hour cultures of Streptococcus Strain SS2 similarly grown in an 8 percent sucrose broth. The activity was measured by determining the amount of glucose released from sucrose by 1 mg. of the enzyme protein. The preparation had five units of the enzyme activity per mg. of protein.

Five test groups of newly weaned and littermated golden hamsters derived from the NIH test colony were placed on the Mitchell diet and their normal flora were depressed by antibiotic treatment in the manner described in Example 1. Group I, the diet control, was neither inoculated nor immunized. Groups II and III were each inoculated with S.mutans Strains 6715 in the manner described in Example 1, Group III being simultaneously immunized with a vaccine-containing dextransucrase and Freund's adjuvant and Group II being immunized solely with Freund's adjuvant. Groups IV and V were inoculated with Streptococcus Strain SS2 (ATCC No. 27006, maintained in the same manner as the S.mutans strain referred to in Example 1); the animals of Group V were simutaneously immunized with a vaccine-containing levansucrase and Freund's adjuvant, while the control hamsters of Group IV were immunized solely with Freund's adjuvant. The inoculation and immunization procedures were carried out in the dosages and at the frequencies referred to in Example 1, the injections of the inoculants and immunogens being administered underneath the chins of the test animals.

After sacrificing the test animals and scoring the caries in the manner described hereinabove, the following results were obtained:

| Group | Cariogenic Inoculation | Immunization | Mean Caries Scores |
|---|---|---|---|
| I (17 animals) | None | None | 5.2 |
| II (9 animals) | S.mutans 6715 | Freund's adjuvant | 26.0 |
| III (15 animals) | S.mutans 6715 | Dextransucrase plus adjuvant | 16.4 |
| IV (9 animals) | Streptococcus SS2 | Freund's adjuvant | 18.2 |
| V (12 animals) | Streptococcus SS2 | Levansucrase plus Freund's adjuvant | 14.0 |

Employing relatively impure enzymes it was thus determined that Group III, the dextransucrase-immunized group, exhibited 38 percent less caries than the control animals which had been inoculated with S.mutans but not immunized (Group II). Similarly, an approximate 23 percent reduction in caries was exhibited in the test group (Group V) locally immunized with the levansucrase-containing vaccine, as compared with the similar control group (Group IV) inoculated with the same microorganism (Streptococcus SS2) but immunized solely with Freund's adjuvant. It is, moreover, believed that the use of purer forms of the dextransucrase and levansucrase enzymes in the test vaccines would result in improved diminution of the mean caries scores.

It should be noted that inconclusive results were obtained in a prior experiment involving both local and systemic immunization of a similar group of test animals with dextransucrase (see Controls K to N in the aforesaid copending application Ser. No. 360,964, which are incorporated by reference herewith). The results obtained in these prior experiments may not, however, properly be subject to interpretation since inoculation of the test animals therein with a cariogenic organism (S.mutans) did not produce an increase in caries formation (compare Test Group L with Diet Control Group K). The inoculating organism may not have had a cariogenic effect on the test animals in this study. Accordingly, the comparative results obtained in the groups subjected to systemic and local immunization in that study (Groups M and N, respectively) may not readily be susceptible of evaluation.

It may be seen from the preceding that, in accordance with the present invention, an improved technique is provided for immunizing animals susceptible to dental caries. It is believed that the method of local immunization hereof results in the production of antibodies of the IgA type in the saliva which neutralizes the activity of the cariogenic Streptococcus organisms or the enzymes capable of forming polysaccharides therewith. The present invention should not, however, be limited by this proposed mechanism of operation, or by the specific embodiments illustrated hereinabove. Accordingly, it should be understood that the preceding description is illustrative and should not be interpreted in a limiting sense.

What is claimed is:

1. In a method for immunization against dental caries, which comprises administering subcutaneously by injection a vaccine, the improvement which comprises locally administering into or near the oral cavity a vaccine constituting an aqueous saline dispersion of an active ingredient selected from the group consisting of (1) a polyglucan polysaccharide elaboration product of a strain of microorganism of the species S.mutans or S.sanguis, and (2) a polyfructan polysaccharide elaboration product of a strain of microorganism within the genus streptococcus, to an animal susceptible to dental caries, said active ingredient being administered in an amount effective for immunization.

2. The method of claim 1 wherein said vaccine is administered into or near the major or minor salivary glands.

3. The method of claim 1, wherein the polyglucan or polyfructan is incorporated in the vaccine in the form of dead cells of the microorganism from which it is elaborated.

4. The method of claim 1, wherein the polyfructan is the active ingredient of said vaccine, the polyfructan incorporating a molecular weight fraction having characteristic infrared absorption peaks at 920 cm.$^{-1}$, 875 cm.$^{-1}$ and 805 cm.$^{-1}$, an intrinsic viscosity at 25° C of from 0.15–0.16, and $[\alpha]_D^{20}$ rotation of 43° to 54°.

5. The method of claim 1, wherein the polyfructan is the active ingredient of said vaccine, said polyfructan being an elaboration product of Streptococcus Strain SS2.

6. The method of claim 1, wherein the polyglucan is the active ingredient of said vaccine, said polyglucan being an elaboration product of S.mutans Strain 6715.

7. The method of claim 1, wherein the vaccine is administered by injection into the chin of the animal to be immunized.

8. The method of claim 1 wherein said vaccine is administered by direct injection.

9. The method of claim 1, wherein the vaccine additionally contains Freund's adjuvant.

10. The method of claim 1, wherein the polysaccharide is administered in the vaccine in an amount equivalent to from 1 to 20 micrograms thereof per kilogram of the body weight of the animal to be immunized.

* * * * *